United States Patent
Peretti et al.

(10) Patent No.: US 12,281,294 B2
(45) Date of Patent: *Apr. 22, 2025

(54) INTERNALLY ILLUMINATED BIOREACTOR

(71) Applicant: Brightwave Partners, LLC, Clarksville, MD (US)

(72) Inventors: Kenneth Paul Peretti, Columbia, MD (US); Timothy Lee Shaw, Clarksville, MD (US)

(73) Assignee: Brightwave Partners, LLC, Clarksville, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/568,035

(22) Filed: Jan. 4, 2022

(65) Prior Publication Data

US 2022/0119754 A1   Apr. 21, 2022

Related U.S. Application Data

(63) Continuation of application No. 17/326,469, filed on May 21, 2021, now Pat. No. 11,214,767.

(Continued)

(51) Int. Cl.
    *C12M 3/00*   (2006.01)
    *C12M 1/00*   (2006.01)
    (Continued)

(52) U.S. Cl.
    CPC .......... *C12M 31/10* (2013.01); *C12M 23/06* (2013.01); *C12M 39/00* (2013.01); *C12M 41/24* (2013.01);
    (Continued)

(58) Field of Classification Search
    CPC ....... C12M 31/10; C12M 39/00; C12M 23/06
    See application file for complete search history.

(56) References Cited

U.S. PATENT DOCUMENTS

2009/0016072 A1   1/2009   Lee et al.
2010/0267125 A1*  10/2010  Erb .................... C12M 27/20
                                              435/292.1
(Continued)

FOREIGN PATENT DOCUMENTS

DE   10 2014 012 217 A1   2/2016

OTHER PUBLICATIONS

European Search Report issued in copending European Patent Application No. 21809213.8 on Oct. 7, 2024.

*Primary Examiner* — Nathan A Bowers
(74) *Attorney, Agent, or Firm* — Whiteford, Taylor & Preston, LLP; Gregory M. Stone

(57) ABSTRACT

Disclosed is an internally illuminated bioreactor, and related algae production methods, that employ integrated in-water grow light assemblies configured to manage the heat generated by lighting elements, such as light emitting diodes ("LEDs") on the in-water grow lights. The bioreactor includes an outer shell and one or more in-water grow light fixtures positioned within the outer shell that are positioned around the perimeter of a hollow, internal tube. The lighting elements and internal tube are themselves contained within a preferably clear, exterior tube of the light fixture that allows light generated by the lighting elements to pass through to the algae culture inside of the growth chamber. A heat management system is provided for cooling the light fixture using forced directed through the hollow, internal tube from the top to the bottom of the tube, out from outlets at the bottom of the internal tube, and upward in the fixture through buoyancy of the warmed air, and thus without additional mechanical air handling devices. As the air moves upward between the lighting elements and the exterior tube, it draws additional heat away from the lighting elements. The warmed air is ultimately exhausted from the top of the lighting fixture. Each lighting fixture preferably also (Continued)

includes a cleaning system that enables the automated cleaning of the outer surface of the exterior tube of the lighting fixture, thus preventing newly formed algae from collecting on the lighting fixture and ensuring a continuous flow of light from the fixture into the algae culture throughout algae production.

14 Claims, 7 Drawing Sheets

Related U.S. Application Data

(60) Provisional application No. 63/028,705, filed on May 22, 2020.

(51) Int. Cl.
*C12M 1/02* (2006.01)
*C12M 1/12* (2006.01)
*F21S 4/28* (2016.01)
*F21V 29/60* (2015.01)
*F21V 29/70* (2015.01)
*F21Y 107/30* (2016.01)

(52) U.S. Cl.
CPC ............... *F21S 4/28* (2016.01); *F21V 29/60* (2015.01); *F21V 29/70* (2015.01); *F21Y 2107/30* (2016.08)

(56) References Cited

U.S. PATENT DOCUMENTS

2011/0107664 A1* 5/2011 Rancis ............... F21V 33/0064
  47/1.4
2012/0129245 A1* 5/2012 Neeb ...................... C12M 41/18
  362/249.02

* cited by examiner

INTERNALLY ILLUMINATED BIOREACTOR

CROSS REFERENCE TO RELATED APPLICATIONS

This application is a continuation of U.S. patent application Ser. No. 17/326,469, filed May 21, 2021, and now U.S. Pat. No. 11,214,767 issued on Jan. 4, 2022, which claims the benefit of U.S. Provisional Application No. 63/028,705 titled "Internally Illuminated Bioreactor," filed May 22, 2020, which application is incorporated herein by reference in its entirety.

FIELD OF THE INVENTION

This invention relates generally to systems and methods for the production and harvesting of biomass, and more particularly to bioreactor systems and related methods for facilitating the production and harvesting of algae.

BACKGROUND

Demand for algal products has grown over recent years to the point at which algae is a significant component of supply chains of human and animal food products, pharmaceuticals and nutraceuticals, and vitamins. With the inclusion of those supply chains comes more stringent quality control and certification requirements. Algae growers need high quality algae, and they need to be able to grow it at an industrial scale.

A variety of systems and methods have been employed in attempts to grow algae for such applications. For example, efforts have been made to grow algae outdoors in shallow ponds or raceways. However, such outdoor growing systems require too large of a geographic footprint, and offer too little production per unit of area, to be able to meet industrial scale requirements. The most effective utilization of land—from a resource management and efficiency perspective—requires large bioreactors or tanks rather than ponds or raceways, for a number of reasons. Outdoor growing is limited by the sun's ability to penetrate shallow pond depths. Outdoor ponds and raceways are typically less than 76 centimeters in depth, and sunlight only penetrates the top few centimeters. A very limited number of areas on the planet are suitable for large-scale outdoor algae growing. Moreover, contamination is a constant threat; wind, rain, and storms can force growers to dump their culture and restart their growing process. Not only does weather affect growth and potentially lower productivity, but just the length of the day likewise limits the culture's exposure to sunlight. These challenges prevent outdoor growers from being able to provide a consistent, predictable supply on the massive industrial scale that is necessary to meet the growing global demand for algal products.

Likewise, efforts have been made to grow algae indoors in bioreactors. For example, indoor bioreactor systems have been configured with a series of closed, clear tubes snaking through a large-scale facility and lit by one or more external grow lights, which systems again suffer from an inability to meet industrial scale requirements. Limitations in current lighting technology can prohibit the use of large tanks. As a result, larger bioreactors today are typically lit externally, with grow lights typically positioned around the outside of a clear bioreactor or tube. When bioreactors or tanks are lit externally, light cannot penetrate through denser cultures. This limits the size and width of the bioreactor, as the algae at the interior regions of a bioreactor that is too large in diameter will not receive sufficient light from the external lights. Additionally, the bioreactor material may change or limit the amount of light that reaches the algal culture, thus limiting the effective size of such bioreactors. Further, currently known indoor bioreactors typically comprise one or more glass tubes that expose the algal culture to one or more grow lights positioned outside of the tubes. Such structure limits the scale to far below any capability of the industrial scale necessary to meet growing algal product demand. Even further, cleaning indoor bioreactors creates even further challenges, as the cleaning process typically requires interrupting production on a regular basis.

In other cases in which attempts have been made to use internal lighting inside of a bioreactor, such efforts have met with only limited success. Increased challenges arise when using interior light assemblies, as the heat that is generated from the lighting fixtures can adversely affect both the temperature of those lighting fixtures (and thus their overall efficiency and durability) and the temperature of the culture, and have thus required complex cooling systems for such internal light fixtures that again have not been suitable for industrial scaling.

Further, while efforts have previously been made to apply algae growth processes to greenhouse gas mitigation and carbon capture and utilization, current approaches to algae growth are not scalable and are not efficient for such applications. More particularly, current outdoor approaches to mitigation are largely expensive and ineffective. Introducing aqueous $CO_2$ requires expensive up-front separation and liquification processes, while gaseous $CO_2$ requires enough culture depth/height to adequately transfer the $CO_2$ to the algal culture. Shallow ponds simply cannot provide this depth. Likewise, current indoor approaches do not have the scale to consistently grow algae on a 24/7/365 basis to consume large quantities of $CO_2$, and typically require production interruptions for cleaning.

Therefore, there remains a need in the art for bioreactor systems and related methods for facilitating the production and harvesting of algae that can readily produce algae at the industrial scale that is necessary to meet the current and future global demand for algal products, and that particularly maximizes algae production for a given space footprint with systems and methods that are less complex and more easily implemented than previously known bioreactor systems and methods.

SUMMARY OF THE INVENTION

Disclosed herein is an internally illuminated bioreactor, and related algae production methods, that avoid one or more of the disadvantages of prior art algae production systems and methods. In accordance with certain aspects of an embodiment, internally illuminated bioreactors are provided having integrated in-water grow lights that efficiently and effectively manage the heat generated by lighting elements, such as light emitting diodes ("LEDs") on the in-water grow lights, and ensure that the heat generated by those lighting elements does not adversely affect the surrounding algae culture or the lighting elements themselves.

With regard to a particularly preferred embodiment, an internally illuminated bioreactor includes an outer shell and one or more in-water grow light fixtures positioned within the outer shell so as to direct light from the light fixtures into an algae growth chamber inside of the outer shell. The light fixture preferably includes an arrangement of vertical lighting elements, such as LED chip assemblies, that are positioned around the perimeter of a hollow, internal tube so as to project light into the growth chamber to stimulate growth of algae in the growth chamber. The lighting elements and internal tube are themselves contained within a preferably clear, exterior tube of the light fixture that allows light generated by the lighting elements to pass through to the algae culture inside of the growth chamber. In order to avoid having the heat generated by the lighting elements adversely affect the algae culture inside of the growth chamber, a heat management system is provided that effectively cools the light fixture while minimizing the need for complex air handling devices. More particularly, forced air is directed through the hollow, internal tube from the top to the bottom of the tube, and exits the internal tube via one or more outlets at the bottom of the internal tube. The air is warmed as it travels through the interior of the internal tube, thus carrying heat away from the lighting elements mounted on the exterior of the internal tube. After the warmed air exits through such bottom outlets of the internal tube, the warmed air travels upwards between the lighting elements and the exterior tube of the lighting fixture through buoyancy of the warmed air, and thus without additional mechanical air handling devices. As the air moves upward between the lighting elements and the exterior tube, it draws additional heat away from the lighting elements. The warmed air is ultimately exhausted from the top of the lighting fixture. Each lighting fixture preferably also includes a cleaning system that enables the automated cleaning of the outer surface of the exterior tube of the lighting fixture, thus preventing newly formed algae from collecting on the lighting fixture and ensuring a continuous flow of light from the fixture into the algae culture throughout algae production.

In accordance with certain aspects of an embodiment of the invention, an internally illuminated bioreactor is provided, comprising an outer shell, a light fixture inside of the outer shell, the light fixture further comprising a light fixture outer tube configured to allow light to pass from the light fixture into a growth chamber inside of the outer shell, a light fixture interior tube having a first flow channel extending from a top of the light fixture interior tube to a bottom of the light fixture interior tube, and at least one outlet from the first flow channel adjacent the bottom of the light fixture interior tube, and a plurality of lighting elements positioned around a perimeter of the interior tube, and a source of forced air in fluid communication with the first flow channel and supplying forced air to the first flow channel, wherein a second flow channel is defined between the plurality of lighting elements and an interior of the light fixture outer tube, the second flow channel receiving warmed air from the at least one outlet and carrying the warmed air from the at least one outlet to a top of the light fixture through buoyancy of the warmed air.

In accordance with further aspects of an embodiment of the invention, an internally illuminated bioreactor is provided, comprising an outer shell defining an algae growth chamber on an interior of the outer shell, a light fixture inside of the algae growth chamber, the light fixture further comprising a plurality of lighting elements positioned around a perimeter of the light fixture, a first air flow channel extending from a top of the light fixture to a bottom of the light fixture, and a second air flow channel extending from the bottom of the light fixture to the top of the light fixture, and a source of forced air in fluid communication with the first flow channel and supplying forced air to the first flow channel, wherein the light fixture is configured to carry air from the first flow channel through the second air flow channel to an exhaust outlet from the light fixture through buoyancy of the air in the second air flow channel and without mechanical air handling devices.

Still other aspects, features and advantages of the invention are readily apparent from the following detailed description, simply by illustrating a number of particular embodiments and implementations, including the best mode contemplated for carrying out the invention. The invention is also capable of other and different embodiments, and its several details can be modified in various obvious respects, all without departing from the spirit and scope of the invention. Accordingly, the drawings and description are to be regarded as illustrative in nature, and not as restrictive.

BRIEF DESCRIPTION OF THE FIGURES

The novel features of the invention are set forth with particularity in the appended claims. A better understanding of the features and advantages of the present invention will be obtained by reference to the following detailed description that sets forth illustrative embodiments, in which the principles of the invention are utilized. The present invention is illustrated by way of example, and not by way of limitation, in the figures of the accompanying drawings, in which like reference numerals refer to similar elements, and in which:

DETAILED DESCRIPTION OF THE PREFERRED EMBODIMENTS

The invention may be understood by referring to the following description and accompanying drawings. This description of an embodiment, set out below to enable one to practice an implementation of the invention, is not intended to limit the preferred embodiment, but to serve as a particular example thereof. Those skilled in the art should appreciate that they may readily use the conception and specific embodiments disclosed as a basis for modifying or designing other methods and systems for carrying out the same purposes of the present invention. Those skilled in the art should also realize that such equivalent assemblies do not depart from the spirit and scope of the invention in its broadest form.

Descriptions of well-known functions and structures are omitted to enhance clarity and conciseness. The terminology used herein is for the purpose of describing particular embodiments only and is not intended to be limiting of the present disclosure. As used herein, the singular forms "a", "an" and "the" are intended to include the plural forms as well, unless the context clearly indicates otherwise. Further-more, the use of the terms a, an, etc. does not denote a limitation of quantity, but rather denotes the presence of at least one of the referenced item.

The use of the terms "first", "second", and the like does not imply any particular order, but they are included to identify individual elements. Moreover, the use of the terms first, second, etc. does not denote any order of importance, but rather the terms first, second, etc. are used to distinguish one element from another. It will be further understood that the terms "comprises" and/or "comprising", or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Although some features may be described with respect to individual exemplary embodiments, aspects need not be limited thereto such that features from one or more exemplary embodiments may be combinable with other features from one or more exemplary embodiments.

Figure 1:
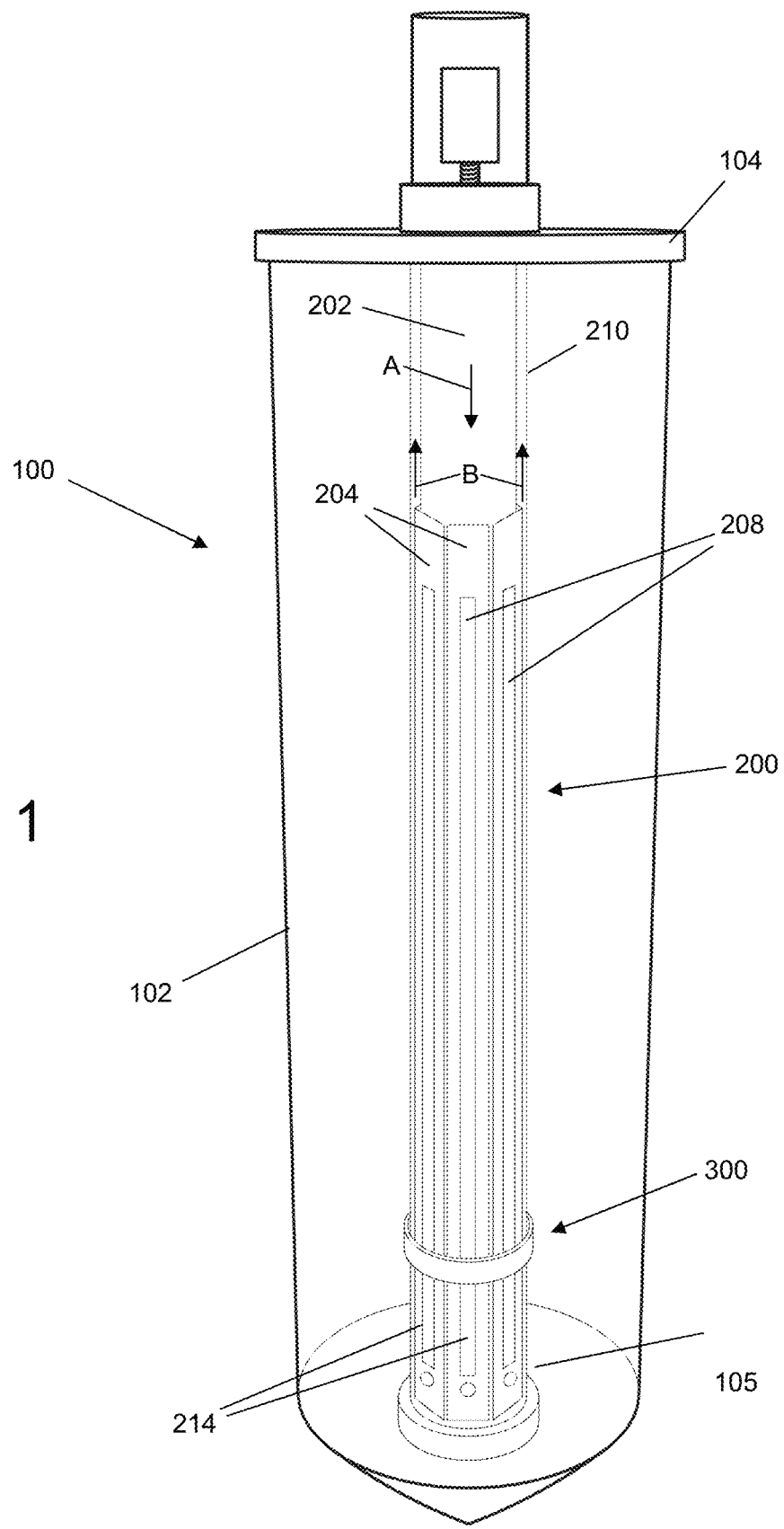
FIG. 1 is a front perspective view of an internally illuminated bioreactor in accordance with certain aspects of an embodiment of the invention.
Figure 2:
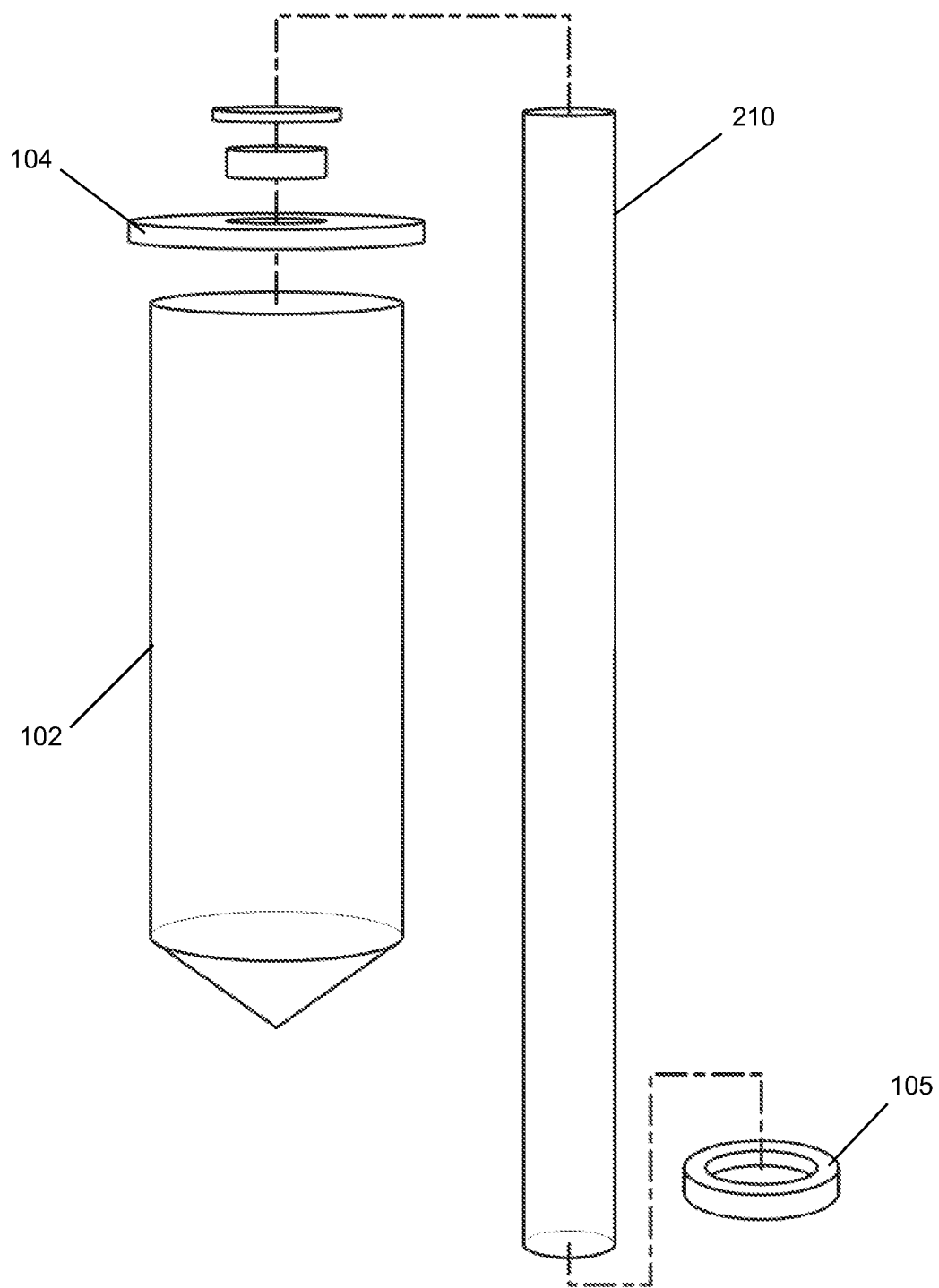
FIG. 2 is an exploded view of components of elements of the bioreactor of FIG. 1 that form an algae growth chamber.

In accordance with certain aspects of an embodiment of the invention, and with particular reference to FIGS. 1 and 2, an internally illuminated bioreactor (shown generally at 100) is provided having integrated in-water grow light fixtures 200 that efficiently and effectively manage the heat generated by lighting elements, such as light emitting diodes ("LEDs") on the in-water grow lights, and ensure that the heat generated by those lighting elements does not adversely affect the surrounding algae culture. In an exemplary configuration, the bioreactor 100 includes an outer shell 102 formed of a lightweight material capable of supporting the desired size and volume of bioreactor 100, such as by way of non-limiting example polyethylene, HDPE, PTFE or other plastics; fiberglass; stainless steel, carbon steel, borosilicate glass, ceramic, and similarly configured materials. In certain exemplary configurations, the material of outer shell 102 is formed of food grade plastic or other material that is capable of meeting certification requirements for food grade materials. Optionally and in certain exemplary configurations, outer shell 102 may be configured with a reflective inner surface that may reflect light generated from the interior grow light fixture back towards the algae culture contained within outer shell 102. A substantially air-tight tank lid 104 may be attached to an open top of outer shell 102 to provide a sealed interior growth chamber 106 that minimizes evaporation and contamination, and preferably allows for precise control of the growing environment. Lid 104 likewise includes ports or openings that allow passage of various elements of the bioreactor into the growth chamber 106, including a central opening for receiving in-water grow light fixture 200, one or more openings for receiving one or more drives for an automatic cleaning system 300 (shown particularly in FIG. 9 and discussed in detail below), and preferably one or more additional openings for one or more of nutrient addition, inbound air and $CO_2$ lines, water addition, and venting. One or more spargers 105 may be provided at the bottom of interior growth chamber 106, which spargers 105 may receive air and/or $CO_2$ from outside of bioreactor 100. Spargers 105 may be arrayed in a number of ways, such as in the form of a ring or other shape surrounding or attached to in-water grow light fixture 200, as linear arrays positioned at various locations at the bottom of growth chamber 106, or otherwise as will readily occur to those skilled in the art to best fit a particular configuration of bioreactor 100, and may in certain configurations include impellers or similar configuration to further aid in moving the sparging gas through growth chamber 106. A drain (not shown) may also be provided at the base of outer shell 102 to allow sampling and/or harvesting of culture from growth chamber 106, and emptying of bioreactor 100. Preferably, an automatic control system is also provided, which (as discussed in greater detail below) provides full monitoring and control of bioreactor 100, preferably via remote access.

Figure 4:
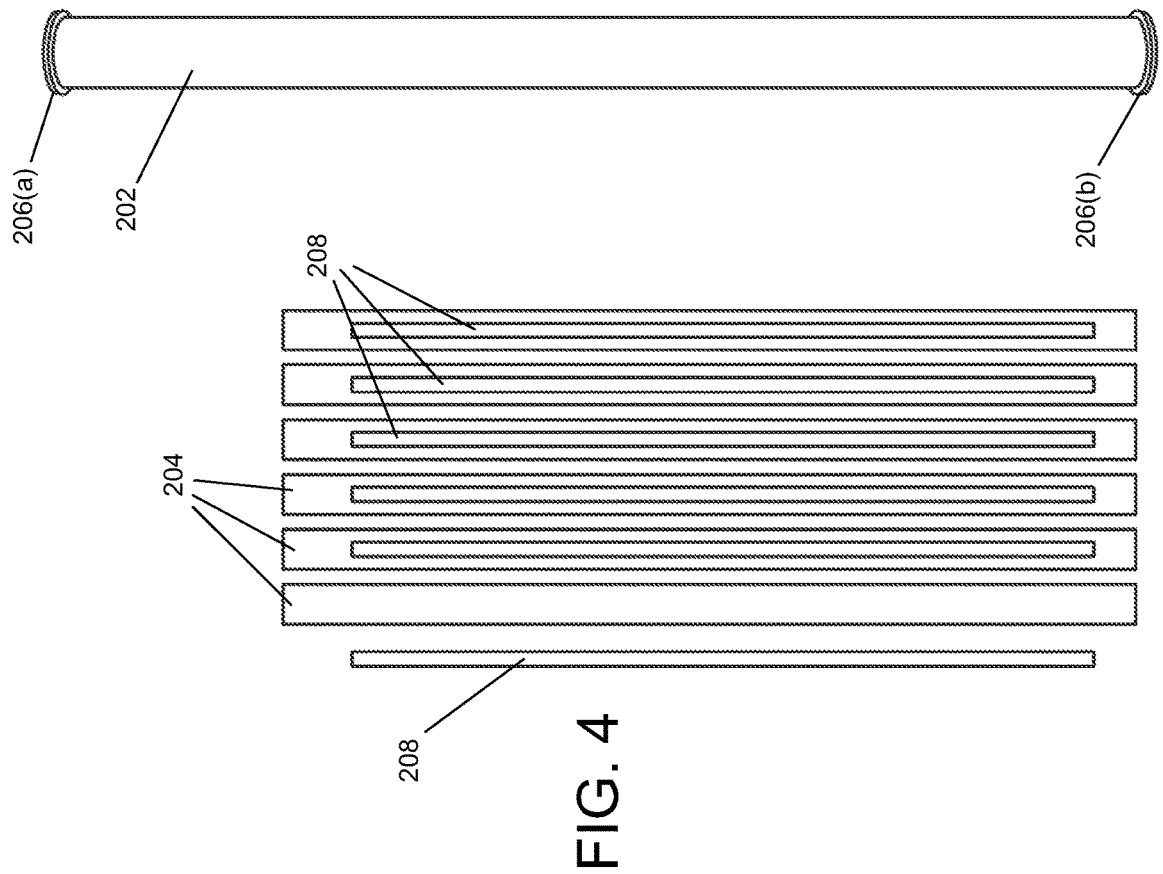
FIG. 4 is an exploded view of the light fixture of FIG. 3.
Figure 3:
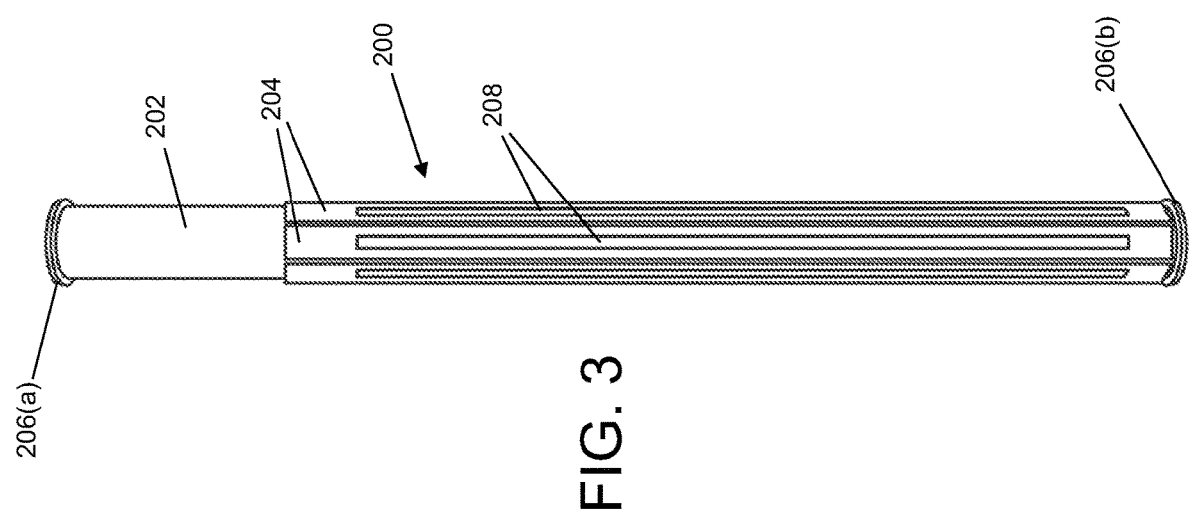
FIG. 3 is a front perspective view of a light fixture for use with the bioreactor of FIG. 1.
Figure 5:
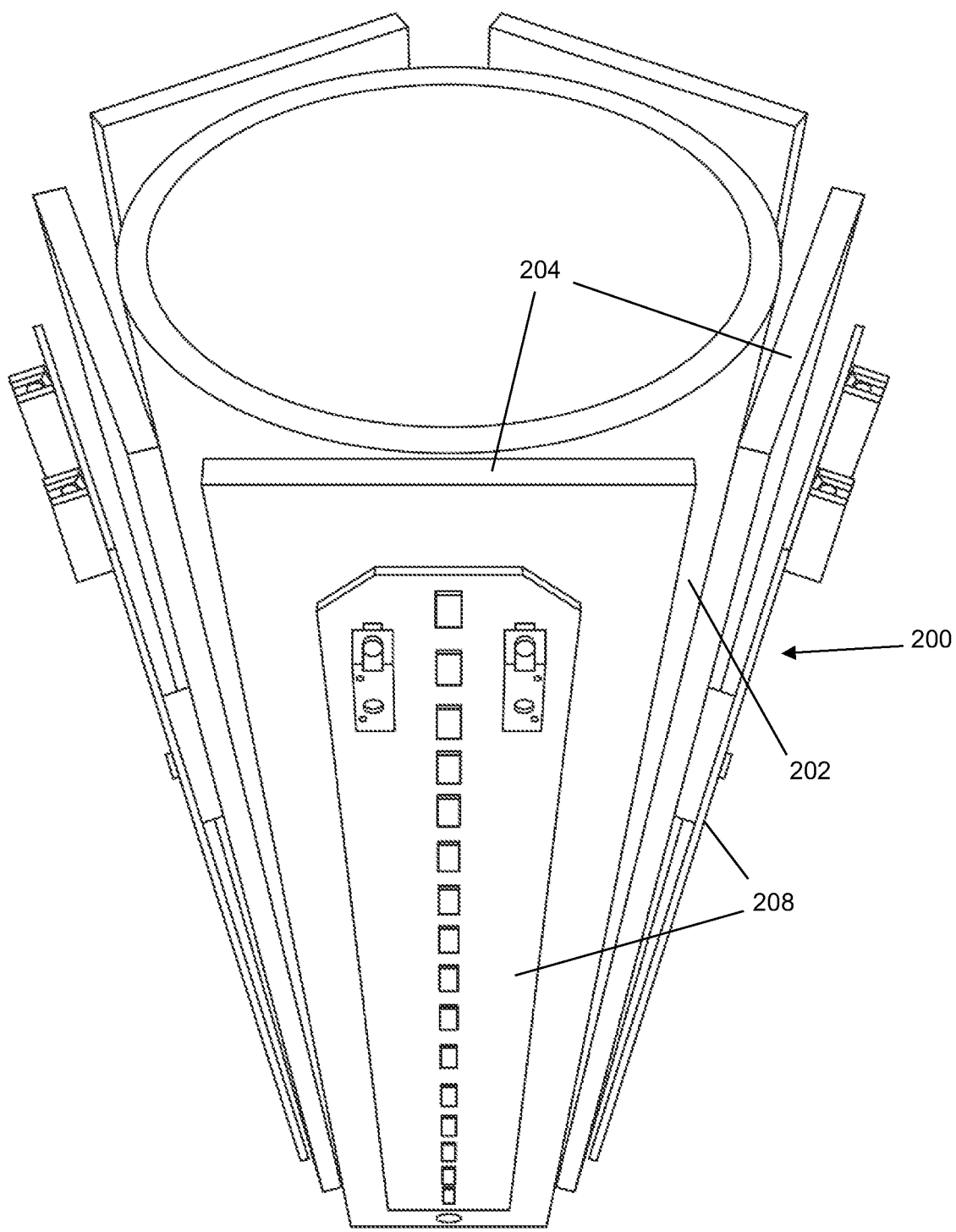
FIG. 5 is a top perspective section view of the light fixture of FIG. 3.

In an exemplary embodiment and as shown in FIGS. 3 and 4 (FIG. 3 showing an assembled in-water grow light fixture 200 and FIG. 4 showing such fixture in an exploded view) and in the close-up, perspective section view of FIG. 5, in-water grow light fixtures 200 include a preferably round, metal, interior tube 202, which in certain configurations is formed of aluminum (in order to provide a lightweight assembly with excellent thermal conductivity and that is cost-efficient). Interior tube 202 forms the core of the in-water grow light fixtures 200, providing structure, strength, heat dissipation properties, and a conduit (comprising the interior space of the hollow round aluminum interior tube 202) that allows forced air to reach the bottom of the interior tube 202. Attached to the exterior of tube 202 are a plurality of metal heat dissipation strips 204, which again are preferably formed of aluminum, with one or more LED chip assemblies 208 affixed to the outer surface of each metal heat dissipation strip 204. Heat dissipation strips 204 extend upward from the bottom of interior tube 202, and terminate at a point on interior tube 202 that is typically at or below the top surface of the culture inside of growth chamber 106. In an exemplary configuration, five heat dissipation strips 204 are mounted on the outside of tube 202 in a symmetrically arrayed pattern, although other numbers of heat dissipation strips 204 may be provided to fit the particular configuration of a given implementation. Each heat dissipation strip 204 contacts that outer surface of tube 202 in a manner to ensure effective heat transfer between the interior tube 202 and the heat dissipation strip 204. By way of non-limiting example, a portion of the exterior of tube 202 may be formed into a flattened region that receives one of heat dissipation strips 204, each of which has a flat rear surface. Alternatively, the rear surface of each heat dissipation strip 204 may have a shallow channel formed therein along the center of the rear of each strip 204 in order to similarly increase the contact surface area between each strip 204 and interior tube 202. Such increased contact area between the interior tube 202 and the flat heat dissipation strips 204 will pull more heat, more quickly, away from LED phosphors positioned on the front surface of each of heat dissipation strips 204, and thus keep them comfortably within their normal operating temperature range. Preferably, and with reference to the top-down section view of FIG. 5, each heat dissipation strip 204 is positioned with respect to interior tube 202 such that forced air moves across the top, along the sides, and along at least part of the bottoms of each heat dissipation strip 204 as it exhausts from apertures near the bottom of the in-water grow light fixture 200 (as discussed in greater detail below). Those skilled in the art will recognize that material compositions and thicknesses may be readily adjusted by those skilled in the art to achieve a particularly desired heat transfer between them based on a particular implementation of bioreactor 100.

Heat dissipation strips 204 may be attached to interior tube 202 via fasteners, such as screws or bolts, or may be welded to interior tube 202, or may be adhesively joined to interior tube 202. In a particular configuration, heat dissipation strips 204 may be joined to interior tube 202 with a thermally conductive epoxy or silicone compound. Such compounds are typically synthetic resins augmented with metallic or inorganic filler materials. Using such optimized thermal interface materials may increase the efficiency of the in-water grow lights and reduces the energy required to keep the grow light operating at a desired temperature. Such epoxies and compounds may exhibit certain advantages over screws, bolts, or welds, such as one or more of (i) providing a higher thermal conductivity and enhanced heat removal, (ii) establishing a larger (and more effective) contact area between heat dissipation strips 204 and interior tube 202, (iii) providing enhanced resistance to shock and vibration, (iv) providing better thermal stability, and (v) providing excellent mechanical strength. Such epoxies and compounds also allow more options than screws, bolts, or welds to allow for spacing between interior tube 202 and heat dissipation strips 204. Variable spacing allows for varying the airflow that moves in the space between the interior tube 202 and the heat dissipation strips 204.

As mentioned above, rows of LED chips 208 (or phosphors) are arrayed along the lengths of heat dissipation strips 204. While the exemplary embodiment discussed herein particularly employs LED chips 208, those skilled in the art will recognize that other high luminosity lighting elements, both now existing and to be developed in the future, may be employed in place of LED chips 208 as disclosed herein, so long as such lighting elements are capable of linear arrangement on heat dissipation strips 204 as discussed herein. In the exemplary configuration discussed herein, LED chips 208 are preferably customizable in a number of ways, including by way of non-limiting example intensity, color, and temperature, in order to maximize growth of a particular strain of algae. Preferably, at least one row of LED chips 208 is provided on each heat dissipation strip 204 (although they may optionally be provided in multiple rows and/or columns and in differing or the same numbers on each heat dissipation strip 204) such that LED chips 208 provide 360° lighting coverage inside of bioreactor 100, with each strip of LED chips 208 exhibiting approximately a 180° diffusion angle. Preferably, LED chips 208 may be dimmed through an automated controller to optimize the light intensity of the LED chips 208 for the current density of the culture inside of bioreactor 100 as detected using in-culture sensors, as discussed in greater detail below.

Figure 7:
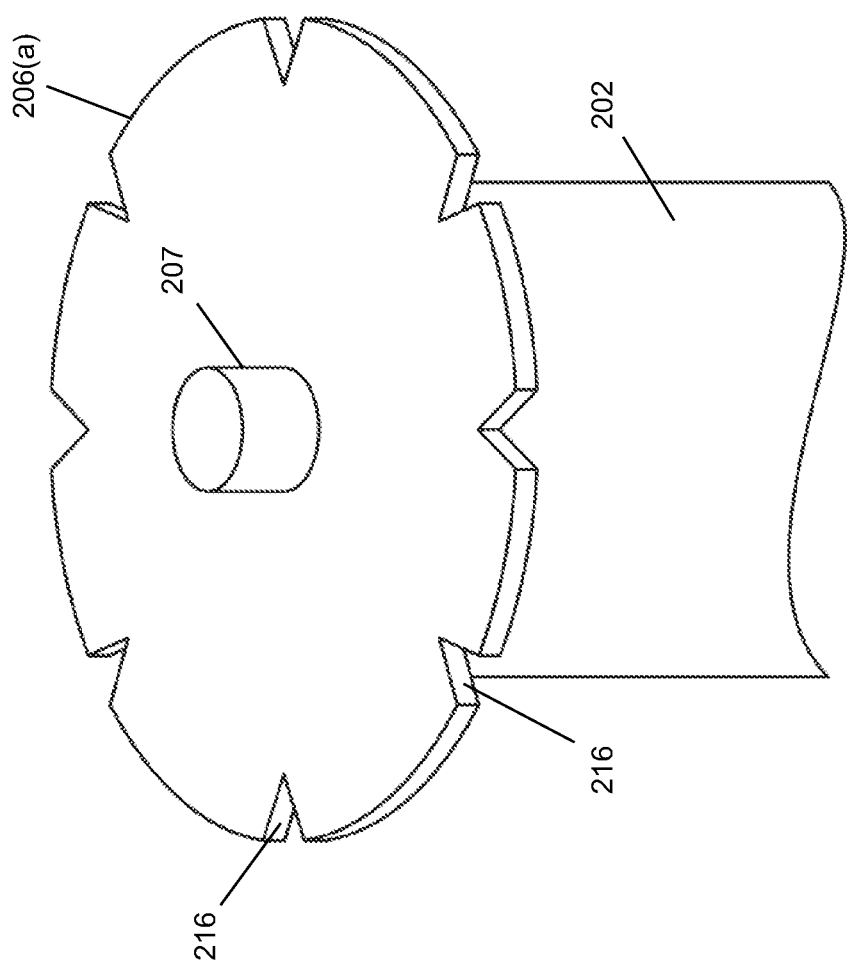
FIG. 7 is a close-up perspective view of the top of the light fixture of FIG. 3.
Figure 6:
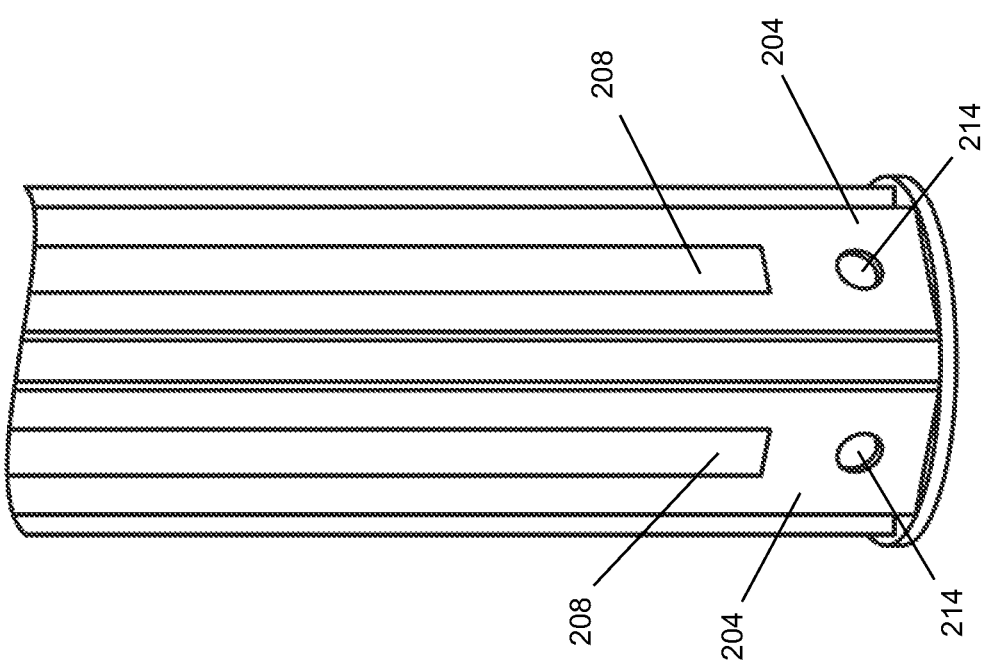
FIG. 6 is a close-up perspective view of the bottom of the light fixture of FIG. 3.

In-water grow light fixtures 200 also include a clear, exterior tube 210 (FIG. 1) that houses interior tube 202 and heat dissipation strips 204. As best shown in FIGS. 6 and 7, metal discs 206(a) and 206(b) are preferably affixed to top and bottom ends, respectively, of interior tube 202, which metal discs 206(a) and 206(b) are preferably formed of the same metal as interior tube 202, such as aluminum to further promote heat dissipation. Discs 206(a) and 206(b) also serve to center and optimally position interior tube 202 and heat dissipation strips 204 within clear, exterior tube 210. More particularly and as shown in FIG. 1, the interior diameter of clear, exterior tube 210 is preferably only slightly larger than the diameter of discs 206 at the top and bottom of interior tube 202, such that in-water grow light fixture 200 is stabilized during use and while it is housed within exterior tube 210. Further, discs 206(a) and 206(b) are preferably sized with respect to interior tube 202 such that the space between interior tube 202 and the heat dissipation strips 204 mounted thereto and the interior of clear, exterior tube 210 is small. In an exemplary configuration, the LEDs on heat dissipation strips 204 may be positioned between 1.25 cm and 5 cm from the interior of the clear, exterior tube 210 in which the respective in-water grow light fixture 200 resides, although other distances may be employed depending upon the overall scale of bioreactor 100.

Top disc 206(a) preferably includes a hole drilled through its center, into which a barb or other inlet 207 is mounted for attachment to a source of compressed air, which compressed air is injected through the top disc 206(a) and into the top of the interior tube 202. Further, top disc 206(a) preferably includes one or more openings 216, such as apertures around the outer edge of top disc 206(a) that are configured to allow heated air within clear tube 210 to escape from the in-water light fixture 200. The apertures 216 in top disc 206(a) are configured and positioned to maximize the flow of air venting from the clear tube 210. The apertures 216 are cut into the top disc 206(a), preferably extending inward from the edge of top disc 206(a). Optionally, in certain configurations bottom disc 206(b) may be wrapped in or provided a bottom, external layer of a cushioning material, which in an exemplary configuration may comprise neoprene or rubber, to provide a cushion or shock absorber between in-water grow light fixture 200 and the bottom interior of outer shell 102 of bioreactor 100, and thus keeping the aluminum of grow light fixture 200 off of and out of direct contact with outer shell 102.

Figure 8:
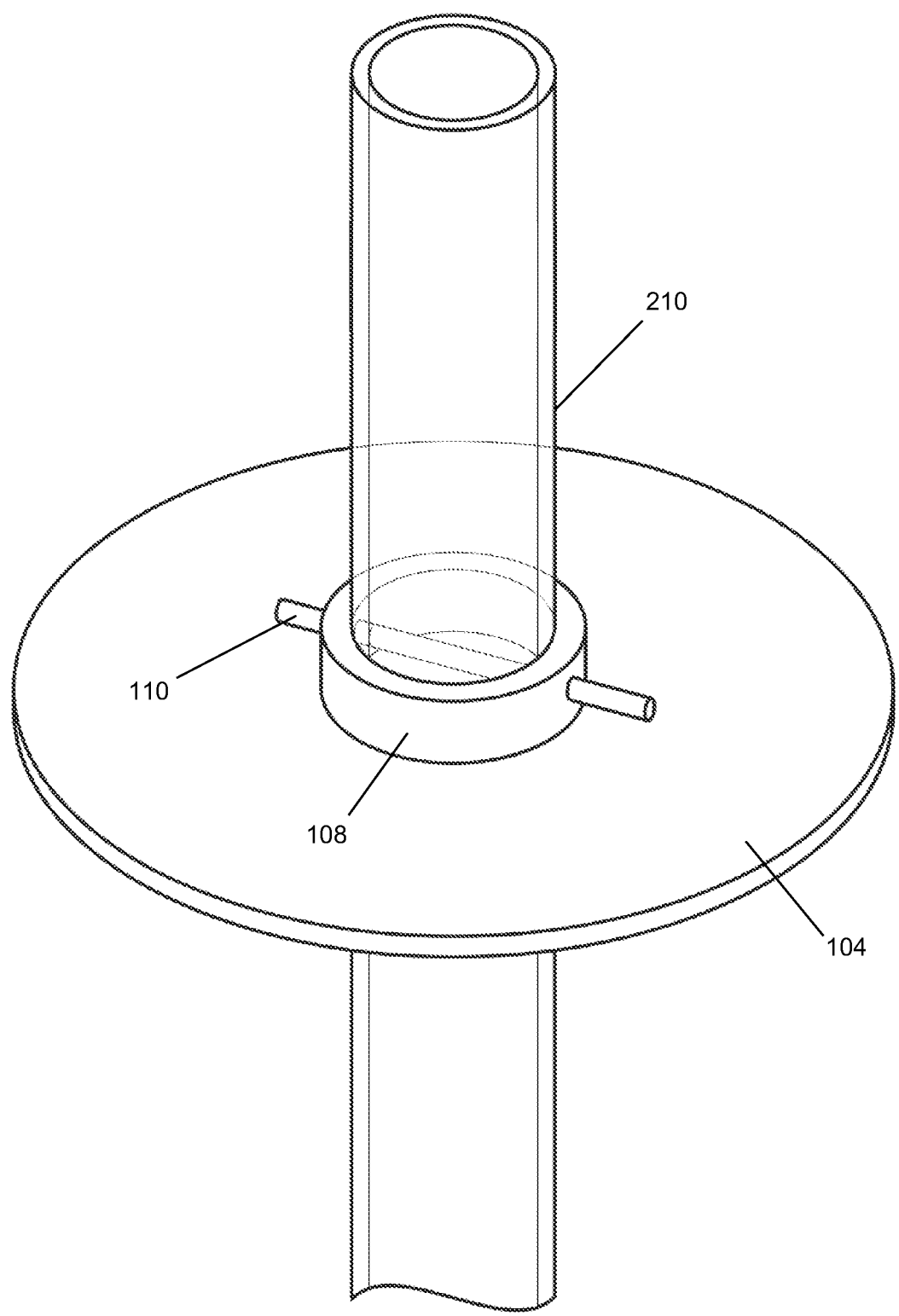
FIG. 8 is a close-up perspective view of a lid assembly for use with the bioreactor of FIG. 1.

Clear, exterior tube 210 of grow light fixture 200 is preferably sealed on its bottom end, and is open on its top end, which top end extends above the top lid 104 of the bioreactor 100, and thus allows access to the LEDs, heat dissipation strips 402, and other elements of grow light fixture 200 when necessary for servicing. Clear, exterior tube 210 is preferably secured to lid 104 of bioreactor 100 by a connecting system that allows its removal for servicing. While many such connecting systems may be employed and configured for a particular configuration by those skilled in the art, an exemplary connecting system may include, by way of non-limiting example and as shown in FIG. 8, a flange collar ring 108 and one or more cotter pins 110 aligned perpendicularly through the flange collar ring 108 to keep the clear, exterior tube 210 securely in place against buoyancy of the in-water grow light fixture 200, and against turbulence in the bioreactor 100. In a particular exemplary embodiment, flange collar ring 108 extends above lid 104 of bioreactor 100 by a distance that is determined by the overall size of the bioreactor 100. For example, a bioreactor 100 with a height of ten feet will require a smaller flange collar ring 108 than a bioreactor 100 with a height of 25 feet or more. The size of flange collar ring 108 is relative to the size of the bioreactor, and thus the size of the in-water grow light fixture 200. Cotter pin 110 may penetrate through the entire flange collar ring 108 and clear, exterior tube 210 to further secure in water grow light fixture 200 in place within bioreactor 100.

Clear, exterior tube 210 is preferably formed of glass or acrylic, or a similarly configured material. One or more clear, exterior tubes 210 with enclosed in-water light fixtures 200 may optionally be provided in a single bioreactor 100, each of which is arranged vertically within bioreactor 100 so that they extend near to the floor of the bioreactor and at a distance from other clear, exterior tubes 210 so that the entire algal culture receives approximately the same level of illumination from in-water light fixtures 200. Thus, a single bioreactor 100, depending upon its size, may include multiple in-water grow light fixtures 200, the number of such grow light fixtures 200 being determined by the ability of the in-water grow light fixture 200 to penetrate into an algal culture, preferably at least 15 cm as measured from the clear, exterior tube 210.

Figure 9:
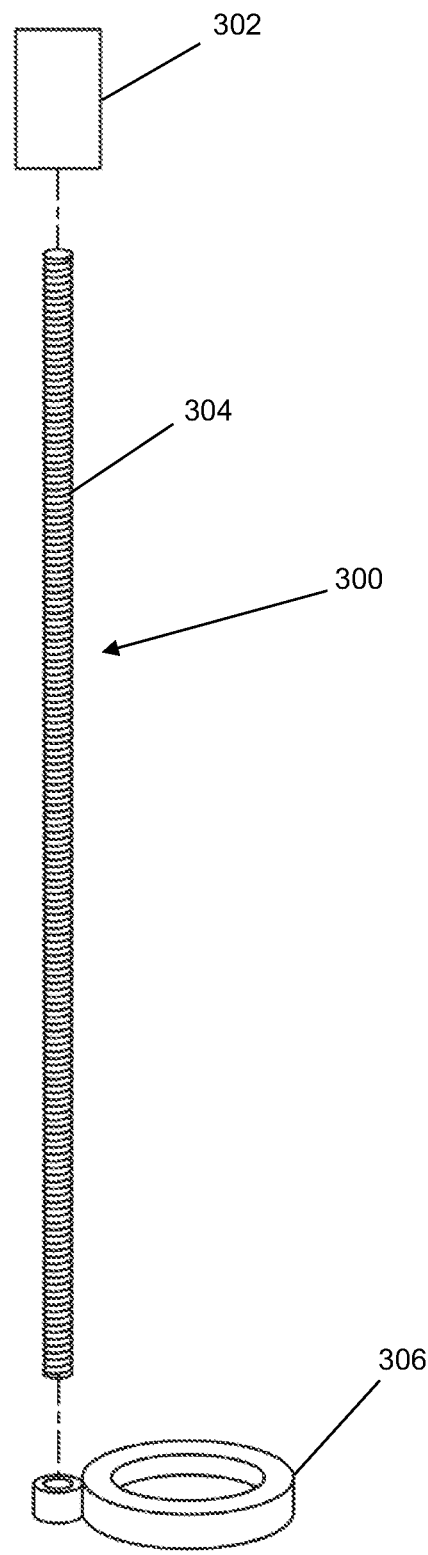
FIG. 9 is an exploded view of a cleaning system for use with the bioreactor of FIG. 1.

In certain exemplary configurations and with reference to FIGS. 1 and 9, bioreactor 100 includes an automatic cleaning system 300 configured to keep the outside of clear, exterior tube 210 free of debris and algal growth, so that the bioreactor 100 can run uninterrupted for as long as possible. This, in turn, prevents algal culture from attaching and aggregating on the clear, exterior tube 210 by scrubbing it through automated movement up and down along the clear, exterior tube 210. In an exemplary configuration, automatic cleaning system 300 includes a motor 302, such as an electric motor, driving a linear actuator 304 that is connected to a cleaning device, such as a scrubbing ring 306. Motor 302 and linear actuator 304 may be mounted to lid 104 of bioreactor 100, such that linear actuator 304 penetrates lid 104 and extends along the entire length of clear, exterior tube 210. Linear actuator 304 (which may comprise, by way of non-limiting example, a worm gear, a belt-driven linear actuator, or other linear actuator assemblies as will readily occur to those of ordinary skill in the art) is attached at its top end to motor 302, and at the bottom to a support bracket (not shown) mounted to the interior of bioreactor 100, which support bracket maintains linear actuator 304, and thus scrubbing ring 306 which is mounted thereto, in close proximity to clear, exterior tube 210. Scrubber ring 306 may be formed, by way of non-limiting example, from PVC or similar material, and may include an interior brushing surface, such as a section of hook-and-loop fastening material, attached to the inner surface of the scrubber ring 306 that contacts and preferably surrounds the outer surface of clear, exterior tube 210. As motor 302 powers scrubber ring 306 up and down the length of the clear, exterior tube 210, the brushing surface on the interior face of scrubber ring 306 moves along the outer surface of clear, exterior tube 210, thus removing any accumulated algae or other matter from clear, exterior tube 210. The automatic cleaning system 300 may be operated via a timer that may schedule cleaning at desired intervals, depending upon culture type and other factors that affect the algal culture's ability to attach to surfaces. While not shown separately in the Figures, those skilled in the art will readily recognize that automatic cleaning system 300 may include other elements, such as a traditional linear drive guide bar and limit switches to reverse direction of scrubbing ring 306 (controlled by motor 302) when scrubbing ring 306 reaches designated points near the top and bottom of exterior tube 210, which other elements may readily be configured by those of ordinary skill in the art for a given exemplary configuration. Likewise, those skilled in the art will recognize that may other actuators for scrubbing ring 306 may be provided to enable it to move back and forth along the length of exterior tube 210 of lighting fixture 200 without departing from the spirit and scope of the invention. Similarly, cleaners other than a complete ring encircling exterior tube 210 may likewise be employed without departing from the spirit and scope of the invention.

As mentioned above, proper thermal management of the in-water grow light fixture 200 is critical to ensure thermal management of the algal culture, and has been a significant impediment to effective bioreactor algal growth at an industrial scale. A sustainable and economically viable cooling process for in-water grow light fixture 200 is therefore quite important to the overall success of a bioreactor system, especially at an industrial scale. If not properly managed and dissipated, heat transmitted by the LEDs on heat dissipation strips 204 will affect the surrounding algal culture, and may render the grow lights either inoperable or may shorten their lives dramatically. Heat must be properly managed and dissipated—it must be quickly removed from the bioreactor for a successful, industrial-scale production system.

To address those thermal management challenges, bioreactor 100 includes a thermal management system that provides cooling of in-water grow light fixtures 200. Through use of such a thermal management system, it is possible to optimize the operating environment of the bioreactor 100 by regulating airflow to speed heat dissipation and create a controlled pressure differential inside and outside of interior tube 202. With particular reference to FIGS. 1, 6 and 7, top disc 206(a) of interior tube 202 preferably includes an inlet 207 positioned at the center of top disc 206(a) providing a cooling fluid inlet into the internal portion of interior tube 202. Of course, as used herein the term "fluid" encompasses a flowable medium, and thus includes gas and more particularly air as the flowing "fluid" cooling medium employed in accordance with certain aspects of the invention. In a particularly preferred embodiment, inlet 207 is in fluid communication with a source of compressed air, which may be injected into the top of interior tube 202. Outlets 214 may be provided along the outer perimeter of interior tube 202 adjacent to its bottom, and particularly just above the bottom round disc 206(b). With this configuration, compressed air is forced through inlet 207 and cools the internal portion of interior tube 202 as it travels downward through a flow channel (shown by arrow A in FIG. 1) inside of the vertical length of interior tube 202. Air escapes interior tube 202 through outlets 214 at the bottom of interior tube 202, and proceeds upward through a second flow channel (shown by arrow B in FIG. 1) comprised of the space between the interior of clear, exterior tube 210 and the outer surface of interior tube 202. As the cooling air travels through that space, it flows upward along the outer surface of interior tube 202, and as best viewed in FIGS. 1 and 5, over and under at least the side portions of heat dissipation strips 204, thus cooling LED chips 208 before the cooling air is exhausted through openings 216 in top disc 206(a). Those skilled in the art will recognize that openings 216 in top disc 206(a) may take on many forms, so long as they allow exhaust cooling air to escape from light fixture 200.

The flow rate of compressed or forced air into in-water light fixture 200 is variable, depending upon the user's lighting requirements, the length and amount of lighting elements provided, and the desired temperature of the algal culture. As will be described in greater detail below, the flow rate of compressed air may be regulated to maintain a desired temperature of the LED chips 208, and to maintain a desired temperature within the clear, exterior tube 210 and within the algal culture itself.

In order to maintain such desired temperatures, airflow velocity or rate (measured in cfm or $m^3/s$) may be increased as light intensity of the in-water grow light fixture 200 is increased. In order to maintain the most effective growth environment inside of growth chamber 106, light intensity should increase as the density of the algal culture increases. As such light intensity is increased, the temperature of the in-water grow light fixture 200 (as measured on the surface of the LED light strip and in the air/space between the outer surface of interior tube 202 and the exterior tube 210 housing it) also increases. Airflow velocity is thus likewise increased to rebalance the temperature around the in-water grow light fixture 200 as light intensity increases. In certain configurations, the air may also optionally be cooled using standard cooling techniques to further aid in evacuating heat from light fixture 200. As discussed in greater detail below, such adjustments may be carried out through use of sensors and an automatic controller.

LED chips 208, although very efficient, do nonetheless generate heat, and transmit heat through their substrates and through empty space via thermal radiation. In the configuration of bioreactor 100 described herein, airflow is thus used to dissipate heat within the interior tube 202 and to minimize radiant heat transfer, or thermal radiation, inside of clear, exterior tube 210. Regulation of such airflow allows proper management and dissipation of all heat generated by LED chips 208, to the point that heat does not adversely affect the desired temperature of the surrounding culture.

Further, the thermal management system configured as described herein creates differential pressure within the in-water grow light fixture 200 which aids in the highly efficient movement of air within in-water grow light fixtures 200 without fans or similar devices. Air, and more preferably compressed air, is forced into the internal portion of interior tube 202, travels downward through interior tube 202, and is forced out of interior tube 202 through outlets 214 at the bottom of interior tube 202. Increasing the volume and pressure in the closed space of the inner portion of interior tube 202 forces the internal air that has been warmed by the LED chips 208 to evacuate. Pressure and other forces then push the warmed air upward through and out of clear, exterior tube 210 (i.e., travelling between the interior of clear tube 210 and the interior tube 202/heat dissipation strips 204/lighting elements 208), such as through air outlet 216 at the top of clear tube 210 (or alternatively through simply an open top end of clear tube 210). The pressure may be monitored and controlled via an automatic controller as discussed in greater detail below.

Further, turbulence of airflow within interior tube 202 is minimized by providing the internal portion of interior tube 202 with a relatively smooth surface, preferably with a consistent cross-sectional area throughout the length of the tube. Thus, air moves quickly through the interior tube 202, from the input barb at the top, toward and through the outlets 214 located at the bottom of the interior tube 202. After heated air exhausts the interior tube 202 via outlets 214 at the bottom, the air then exhausts toward the top of the clear, exterior tube 210 via thermal buoyancy—working its way over, under, and around the heat dissipation strips 204 attached to the outside of the interior tube 202. Flow path turbulence is thus increased on the outer surface of the interior tube 202 due to the presence of heat dissipation strips 204. Optionally, the cross-sectional area of interior tube 202 may alternatively decrease as airflow moves downward through the interior tube 202. Because fluid flow speeds up as cross-sectional area of the interior tube 202 decreases, the interior tube 202 and in-water grow light fixture 200 overall may exhaust and cool more quickly. Such a configuration may be particularly preferable in configurations of bioreactor 100 that are longer in length, such as those employing in-water grow light fixtures 200 of lengths of 6 meters or more, as may be used in larger bioreactors.

While the foregoing description includes particularly compressed air being delivered to the interior of interior tube 202, in other exemplary configurations of bioreactor 100 that are of relatively small scale (e.g., a total volume of 1000-1500 liters, for example), fewer lighting elements 208 will result in less heat being generated, and thus a lower cooling demand. In such configurations, a fan or similarly configured source of forced air may be provided to, as above, push air into the interior of interior tube 202 to create the cooling airflow discussed above. Also in such smaller scale configurations, top disc 206(a) be optionally be eliminated altogether.

The compressed and/or forced air that is supplied to in-water grow light fixture 200 is preferably dry air having minimal humidity, as the air is used to cool an array of electronic components inside of in-water grow light fixture 200. Air supplied to in-water grow light fixture 200 is preferably dried at its source, but alternatively could be dried prior to injection into in-water grow light fixture 200 using in-line filters and drains.

In accordance with further aspects of an exemplary embodiment of the invention, after a desired amount of algae has been produced in bioreactor 100, algae may be drained and harvested from the bottom of the bioreactor 100. This allows gravity to perform the bulk of the work in carrying algal culture to the drain of bioreactor 100. If bioreactor 100 is equipped with a generally cone-shaped bottom, then the drain is preferably located at the bottom of the cone. If bioreactor 100 is equipped with a flat exterior bottom, then the drain is preferably located at the bottom of a side of the outer shell 102 of bioreactor 100, and a slanted false bottom or the like may be provided on the interior of bioreactor 10 to allow settled algae to naturally move toward the drain. In either case, both drain positions provide the lowest energy solutions for placement of a drain in bioreactor 100. While no pumps are necessary in order to drain a bioreactor 100 configured as described above, a pump could optionally be employed to speed the draining process.

A controller may be provided to regulate the operation of bioreactor 100 on an automated basis via an interface that integrates the operating systems of, for example, off-the-shelf sensors and software. More particularly, and as discussed in greater detail below, the growing environment inside of bioreactor 100 may be automatically regulated by monitoring and maintaining strict control over specific key variables known to affect algal production, including culture temperature, light intensity, pH, flow rates, nutrient levels, and air/gas flow. Data that is tracked by individual sensors in bioreactor 100 is collected and may be pushed through a central dashboard and analyzed, and may be integrated with data from other bioreactor sensors to ensure that pre-programmed settings are maintained throughout the bioreactor. Preferably all of such data may be viewed remotely, such as through an Internet connection. Additionally, controls may be activated or overridden remotely. Finally, bioreactor 100 may be equipped with alarms that can be heard and/or monitored remotely, e.g., via a mobile telephone, tablet, or computer.

The controller may receive data from temperature sensors positioned to monitor the temperature of LED chips 208. The LED chip temperature sensor may be mounted on the LED board next to the LED chips 208, which LED boards are mounted on the flat heat-dissipating strips 204, in order to provide the controller with the real-time operating temperature of the LED chips 208. The controller may also receive data from temperature sensors positioned to monitor the temperature of the algal culture (in-water). The temperature of the algal culture may be monitored with a temperature sensor to ensure that the culture maintains a specifically desired temperature or stays within a specific tight range of temperatures. Each strain of algae grows best at a particular optimal temperature or within a particular optimal temperature range, and the controller may be configured to regulate other elements of the bioreactor (as discussed further below) to ensure that such optimal temperature or temperature range is maintained. A fail-safe switch may be provided in communication with the LED chip temperature sensor, and optionally the algal culture temperature sensor, to ensure that the in-water grow light fixture 200 is turned off in the event that the LED board temperature exceeds, by way of non-limiting example, 75° C., which additionally preserves the LED chips 208 and related electronics in the event of a failure in the airflow supply. The automation system may likewise be configured to send an alarm to preset phones, tablets, computers, or other remote devices to alert a technician or other individual that the LED board temperature has exceeded 75° C., and may similarly cause alarms to generate alerts if the temperature reaches preset values lower than 75° C. Further, one or more temperature sensors may be provided in the air/space between the LED chips and the interior of clear, exterior tube 210 to ensure that the air in direct contact with the clear, exterior tube 210 (which in turn is in direct contact with the algal culture) is maintained within a desired temperature range.

The automation system is preferably configured to control three primary elements of the algal growth environment that affect culture temperature: namely, temperature of the light fixture, the amount of airflow into spargers, and the ambient air temperature. More particularly, regarding the temperature of the light fixture, the controller may modify the amount of airflow to the fixture 200 in order to cool or heat the fixture, and thereby cool or heat the algal culture to a particularly desired temperature. Likewise and regarding airflow into spargers at the bottom of growth chamber 106, the controller may monitor the temperature of the algal culture directly and automatically adjust the flow of air to the spargers, thus distributing gas or air directly into the algal culture as a secondary measure to affect the culture's temperature. Further and regarding ambient air temperature, the controller may adjust surrounding room temperature through connection to room heating and cooling equipment as yet another measure to cool or heat the algal culture in bioreactor 100.

The controller may further monitor one or more humidity sensors positioned to detect the moisture level in the air supplied to in-water light fixture 200. In the event that the detected moisture level exceeds a predetermined level, the controller may automatically shut down in-water grow light fixture 200, and alarms may be sent to preset devices as discussed above to alert them to the increased moisture level and to allow for the same to be investigated.

The controller may also monitor the density of the culture inside of bioreactor 100 via in-water light intensity sensors placed throughout the bioreactor. Dependent upon the desired settings, the controller may monitor density and light intensity readings and control the light intensity of the in-water grow light fixture 200 to create the optimum level of light intensity through the culture.

Further, the controller may monitor the pH of the algal culture inside of bioreactor 100 via in-water sensors, and control the pH level by injecting $CO_2$ into the culture until the appropriate pH level is reached and maintained. In exemplary configurations, the controller may be configured to maintain any desired pH levels, such as pH levels in the range of 9-10 for high growth, or possibly in the range of 5-7 for industrial-scale mitigation of greenhouse gases. The controller may further send an alarm to preset devices as discussed above to alert them if the pH exceeds, or drops below, a predetermined threshold level.

Still further, the controller may monitor the conductivity and oxidation reduction potential ("ORP") of the culture, and may control and/or apply the proper amount of nutrient via either slow-drip or batch delivery. The controller may further send an alarm to preset devices as discussed above to alert them if a malfunction occurs in the nutrient delivery system.

Even further, the controller may direct the air regulators to finely inject more air and/or $CO_2$ through the spargers and into the culture at the bottom of the bioreactor to control the movement of the algal culture inside of growth chamber 106. Such continuous movement of the culture inside of the growth chamber 106 may be important in overall culture growth, as continuous movement of the culture ensures the entire algal culture receives equal exposure to the light being emitted by the in-water grow light fixtures 200, and likewise inhibits algal buildup on the clear, exterior tube 210 of the in-water grow light fixtures 200 (which buildup can diminish the fixture's effectiveness) and buildup on the outer walls of the growth chamber 106.

The controller may also communicate with algal growth density sensors in order to automatically activate a harvesting mechanism in the drain of the bioreactor 100. A density sensor reading may show that algal growth has reached its greatest extent; before the growth rate of the mature culture can settle and plateau, the drain of the bioreactor 100 may be activated and opened to drain a pre-determined volume of culture from the growth chamber 106. A pipe attached to the drain preferably transports the harvested culture to a collection point where it may then be processed. Once a volume of culture is drained from the bioreactor, the controller may add an equal volume of fresh, treated (to the extent necessary) water to the bioreactor 100 from the top. Optionally, the controller may manage either or both of batch harvesting at designated times or algae production volumes being reached, or continuous harvesting. Likewise, the controller may add an appropriate amount of nutrient, depending upon the volume of water added and the time since the last nutrient administration. The controller may further send an alarm to preset devices as discussed above to alert them if a malfunction occurs during the harvesting process.

Finally, the controller may activate automatic cleaning system 300 to cause scrubbing ring 306 to move up and down the clear, exterior tube 210. Such activation of automatic cleaning system 300 may occur on a regular, timed basis, or it may activate automatically if and when the light intensity sensor reading falls below a predetermined threshold level. Settings for automatic cleaning system 300 may vary based on the algal strain that is grown in the bioreactor 100. Some strains may require vigorous scrubbing, while other strains may require little or no scrubbing. The function of the automatic cleaning system 300 as described herein is to keep the bioreactor running uninterrupted for as long as possible. The controller may further send an alarm to preset devices as discussed above to alert them if a malfunction occurs during the cleaning process.

In using a bioreactor configured as above for the production of algae, it may be preferable to prepare the water in which the algae is to be grown in growth chamber 106. Generally, there are a variety of ways to appropriately prepare water that will be used to start and maintain a bioreactor. Some growers may treat the water with bleach or ozone or another cleaning agent prior to inoculation. Using reverse osmosis water is another method that may be used, and it does not present the risk of killing the algae as bleach might if it is not properly diluted. The water preparation method chosen by the grower likely has much to do with what is most convenient or cost-effective for that particular location. However, bioreactors configured in accordance with the foregoing disclosure may be built anywhere, and thus do not impose a particular water preparation method on the bioreactor user. Rather, a bioreactor configured in accordance with the foregoing disclosure may employ any water preparation method, with all prepared water injected into the bioreactor 100 optionally through a dedicated port on the lid 104 of the bioreactor 100.

Bioreactors configured in accordance with the foregoing disclosure may provide a number of improvements over prior art systems and methods for the production of algae. For example, a bioreactor configured as above may provide complete and homogeneous light penetration throughout the entirety of large-diameter bioreactors and tanks (e.g., those having a diameter of greater than one meter). The ability to properly illuminate tanks or bioreactors from within allows for the utilization of larger tanks than were previously considered, such as in systems that would utilize sunlight or grow lights placed outside of the bioreactors. Further, using internally lighted, large tanks or bioreactors may optimize the footprint of an indoor or outdoor grow facility, particularly when considering both cubic feet and square feet, and may serve to minimize the footprint relative to production capacity. This factor may allow growers to truly maximize the productivity of an available footprint, thus providing a key efficiency factor that may be required for scaled, industrial-level indoor growth to be cost effective. Bioreactors configured in accordance with the foregoing disclosure may thus be scaled to any size, and can be built and operated essentially anywhere—in any external environment, and they can be fitted to any available footprint.

Still further, a bioreactor configured as above may ensure that heat energy created by providing the appropriate amount of light to a large culture does not overheat that culture. More particularly, the thermal management system may allow the in-water grow light fixtures 200 to be completely submerged into a liquid culture without transferring heat to the culture and while keeping the operating temperatures of the in-water grow light fixtures at an optimal temperature to preserve durability and reduce the likelihood of overheating. Even further, a bioreactor configured as above may substantially prevent algal detritus from building up on clear, exterior tube 210 surrounding the in-water grow light fixtures 200, which could otherwise tend to diminish light intensity, and may avoid the need to interrupt algal production on a regular basis to clean the interior of the bioreactor.

Likewise, bioreactors configured as above may offer an optimum growth environment for algae by automatically controlling and/or regulating five primary factors that affect algae growth—namely, light intensity/spectrum, pH, temperature, nutrient, and air/culture flow.

Having now fully set forth the preferred embodiments and certain modifications of the concept underlying the present invention, various other embodiments as well as certain variations and modifications of the embodiments herein shown and described will obviously occur to those skilled in the art upon becoming familiar with said underlying concept. It should be understood, therefore, that the invention may be practiced otherwise than as specifically set forth herein.

What is claimed is:

1. An internally illuminated bioreactor, comprising:
an outer shell containing a volume of water defining a growth chamber;
a light fixture inside of said outer shell and immersed in the water, said light fixture further comprising:
 a light fixture outer tube configured to allow light to pass through said light fixture outer tube into the growth chamber, wherein the growth chamber is further defined by the water between an interior of the outer shell and the exterior of the light fixture outer tube;
 a light fixture interior tube having a first flow channel extending from a top of said light fixture interior tube to a bottom of said light fixture interior tube, and at least one outlet from said first flow channel adjacent said bottom of the said light fixture interior tube; and
 a plurality of lighting elements positioned around a perimeter of said interior tube; and
a source of forced air in fluid communication with said first flow channel and supplying forced air to said first flow channel;
wherein a second flow channel is defined by said outer perimeter of said interior tube and an interior side of said light fixture outer tube, said second flow channel receiving warmed air from said at least one outlet and carrying said warmed air from said at least one outlet to a top of said light fixture through buoyancy of said warmed air, and wherein said first flow channel and said second flow channel together form a bidirectional, vertical cooling flow path through said internally illuminated bioreactor from a top of the internally illuminated bioreactor inside of said light fixture interior tube, out of a bottom of said light fixture interior tube, and upward between said light fixture interior tube and said light fixture outer tube.

2. The internally illuminated bioreactor of claim 1, wherein an interior of said outer shell defines a growth chamber, wherein said light fixture is positioned centrally inside of said growth chamber.

3. The internally illuminated bioreactor of claim 2, wherein said internally illuminated bioreactor includes only a single said light fixture providing an unobstructed light path from said single light fixture to an interior surface of said outer shell.

4. The internally illuminated bioreactor of claim 1, wherein said light fixture is further configured to carry said warmed air from said at least one outlet to the top of said light fixture without mechanical air handling devices.

5. The internally illuminated bioreactor of claim 1, further comprising a moveable cleaning device in contact with an exterior of said light fixture outer tube, and a motor in driving engagement with said cleaning device and configured to move said cleaning device along a vertical length of said light fixture outer tube.

6. The internally illuminated bioreactor of claim 5, said cleaning device further comprising a ring moveably mounted on a linear drive, wherein said linear drive is engaged with said motor.

7. The internally illuminated bioreactor of claim 6, said ring further comprising a brushing surface on an interior perimeter of said ring, wherein said brushing surface is in contact with the exterior of said light fixture outer tube.

8. The internally illuminated bioreactor of claim 1, said light fixture further comprising a plurality of heat dissipation strips affixed to an exterior surface of said light fixture interior tube, wherein said lighting elements are affixed to an outer face of each of said heat dissipation strips.

9. The internally illuminated bioreactor of claim 8, wherein each said heat dissipation strip further comprises a planar strip, wherein a mid-portion of a back side of each said planar strip is affixed to said exterior surface of said light fixture interior tube, and edge portions of each said back side of each said planar strip are positioned away from said exterior surface of said light fixture interior tube.

10. The internally illuminated bioreactor of claim 1, wherein said source of forced air further comprises a source of compressed air that delivers forced air to said first flow channel without mechanical air handling devices.

11. The internally illuminated bioreactor of claim 10, said light fixture interior tube having a top disc in sealing engagement with a top end of said light fixture interior tube and a compressed air inlet extending through said to disc.

12. The internally illuminated bioreactor of claim 11, said top disc having a diameter that is greater than a diameter of said light fixture interior tube.

13. The internally illuminated bioreactor of claim 12, said top disc having at least one warmed air outlet extending through said top disc and in fluid communication with said second flow channel and an air outlet of said light fixture outer tube.

14. The internally illuminated bioreactor of claim 1, wherein said source of forced air further comprises a fan configured to direct air into said first flow channel.

* * * * *